US008481062B2

(12) United States Patent
Vargas Arispuro et al.

(10) Patent No.: US 8,481,062 B2
(45) Date of Patent: Jul. 9, 2013

(54) **MIXTURE AND METHOD FOR CONTROLLING THE INSECT *ACROBASIS NUXVORELLA* ON *CARYA ILLINOIENSIS* PLANTS**

(75) Inventors: Irasema del Carmen Vargas Arispuro, Sonora (MX); Miguel Angel Martínez Téllez, Sonora (MX); María Alba Guadalupe Corella, Carretera a la Victoria Km (MX)

(73) Assignee: Centro de Investigacion en Alimentacion y Desarrollo A.C., Hermosillo, Sonora (MX)

( * ) Notice: Subject to any disclaimer, the term of this patent is extended or adjusted under 35 U.S.C. 154(b) by 83 days.

(21) Appl. No.: 12/998,563

(22) PCT Filed: Nov. 3, 2008

(86) PCT No.: PCT/MX2008/000149
§ 371 (c)(1),
(2), (4) Date: Jun. 27, 2011

(87) PCT Pub. No.: WO2010/050791
PCT Pub. Date: May 6, 2010

(65) Prior Publication Data
US 2011/0251292 A1 Oct. 13, 2011

(30) Foreign Application Priority Data

Nov. 3, 2008 (MX) .................... MX/a/2008/014015

(51) Int. Cl.
*A01N 25/00* (2006.01)
*A01N 59/04* (2006.01)
*A01N 27/00* (2006.01)

(52) U.S. Cl.
USPC ............................ 424/405; 504/101; 514/919

(58) Field of Classification Search
None
See application file for complete search history.

(56) References Cited

U.S. PATENT DOCUMENTS

| 5,521,165 A * | 5/1996 | Warren et al. ................... 514/64 |
| 7,230,033 B2 * | 6/2007 | Dolan et al. .................. 514/691 |
| 2005/0171213 A1 * | 8/2005 | Zhu et al. ...................... 514/690 |

FOREIGN PATENT DOCUMENTS

WO WO 9848625 A1 * 11/1998

OTHER PUBLICATIONS

Mahmoud M. M. Soliman, Phytochemical and toxicological studies of *Artemisis l.* (Compositae) essential oil against some insect pests, Archives of Phytopathology and Plant Protection, Apr. 2007, 40(2), 128-138.*
M. Lawrence Henneman, Response to Walnut Olfactory and Visual Cues by the Parasitic Wasp *Diachasmimorpha juglandis*, Journal of Chemical Ecology, Nov. 2002, 28 (11), pp. 2221-2244.*
Israel L. Andrade, Chemical Composition and Insecticidal Activity of Essential Oils from *Vanillosmopsis pohlii* Baker against *Bemisia argentifolii*, J. Agric. Food Chem., Aug. 2004, 52, pp. 5879-5881.*
Mody, N., et al., Volatile Components of Pecan Leaves and Nuts, *Carya illinoensis* Koch J. Agric. Food Chem., 1976, vol. 24 (1), pp. 175-177.
SAES-422:S1017, Improved Systems for Management of Economically-Important . . . , Jan. 19, 2009, <URL: http://www.minss.umd.edu/homepages/saes.cfm?trackID-6817.

* cited by examiner

*Primary Examiner* — Melenie McCormick
*Assistant Examiner* — Andrew Lee
(74) *Attorney, Agent, or Firm* — Hudak, Shunk & Farine Co. LPA

(57) ABSTRACT

The invention consists of a mixture of organic chemicals avoiding the use of insecticides, and a method for pest control based on the mixture consisting in bringing about the premature eclosion of the hibernating larva and its possible death through inanition; experimentation has demonstrated it to be effective in bringing about the premature eclosion of the pecan nut casebearer or *Acrobasis nuxvorella* (Lepidoptera: Pyralidae) on pecan trees (*Carya illinoiensis*). The objective is to provide an ecological method for controlling pests such as the pecan nut casebearer, in this manner reducing or avoiding the use of inorganic chemical insecticides which have a significant impact on the environment.

5 Claims, 1 Drawing Sheet

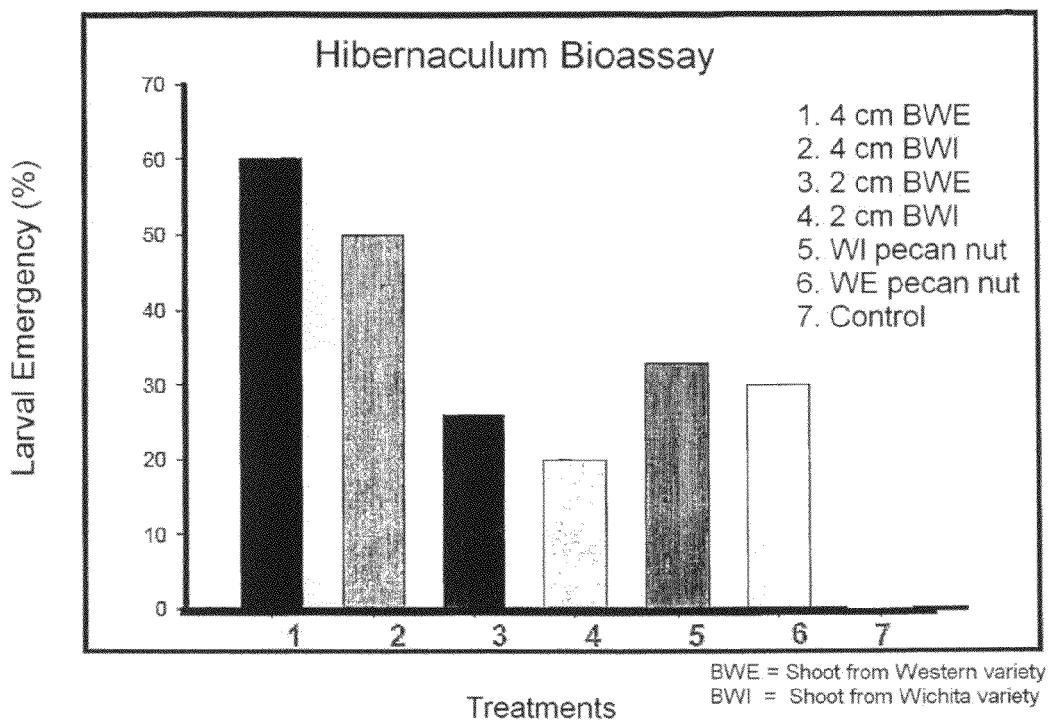

MIXTURE AND METHOD FOR CONTROLLING THE INSECT *ACROBASIS NUXVORELLA* ON *CARYA ILLINOIENSIS* PLANTS

TECHNICAL FIELD

The present invention relates to the field of biotechnology to control pests affecting crops.

BACKGROUND

One of the major insect pests infesting pecan nut trees (*Carya illinoiensis*) from northern Mexico and southern United States is the pecan nut casebearer or *Acrobasis nuxvorella* (Lepidoptera: Pyralidae). When not properly controlled this pest causes more than 40% loss of nut clusters.

Pecan nut casebearer completes three to four generations per year. The process begins in the early spring when the winter larvae emerge from their cocoons and feed on young buds and shoots of pecan nut tree. Later, the mature larva pupate in the cracks and creases of the bark or in tunnels in the shoots. Moths from these overwintering larvae oviposit the eggs of the first generation in the young nuts.

The newly hatched first generation larvae do not feed directly from the nutlets, but feed on the buds for a period of two to four days, during which they are exposed to the action of insecticides. Therefore, the control should focus on this stage of the pest, because once they are inside the nut, the larvae are protected from insecticide treatments. These first generation larvae are the ones having the highest population density and causing major economic losses. A single larva can destroy many nuts and even the entire cluster in order to complete its development. The following two generations are less numerous and cause less damage to the crop yield, because by this time the nuts are larger and one larva completes its development on a single nut or the nuts may not be susceptible to the pest attack. Therefore, the phytosanitary control is directed primarily to the first generation.

At the onset of fall, the larvae from last generation prepare to enter diapause or hibernation and migrate to the base of a dormant bud where they build a silk cocoon called a hibernaculum in which they will spend the winter.

Development of this overwintering stage is affected by the temperatures of autumn and winter. A report from INIFAP-Mexico Seminar on pecan nut tree in April 2007 showed an unusually low density of hibernating larvae as a probable consequence of the deaths caused when temperatures reached 95° F. (35° C.) in the fall-winter 2005. It is believed that the worm diapause ends when the pecan nut tree gets out of its dormant state. It is at this point that the worm hatches from the hibernaculum and feeds on buds and young shoots.

Control of this pest is based on two methods: 1) accumulation of heat units (HU) from shooting and 2) monitoring with pheromone traps, which can establish the appropriate time an insecticide will be applied to the newly hatched larvae and before entering the nut.

To predict the moment in which the oviposition of the first generation will occur, the pecan nut producers caught moths using pheromone traps, or they determine the daily heat units in the spring. The accumulation of heat units begins 10 days before sprouting of 50% of the buds. According to Harris (1995) and Harris and Dean (1997) the appropriate time of control is the date when 1,831 HU>38° F., equivalent to 1,019 HU>3.3° C. had accumulated, which is the physiological time required for the occurrence of pupation, adult emergence, oviposition, hatching and first larval entrance into nutlets. The daily heat units are determined as follows:

Daily HU=[(Maximum Temperature+minimum Temperature)/2]−basal Temperature wherein basal temperature is 38° F. (3.3° C.).

Once the appropriate time of control is determined, it is necessary to know if the pest population is capable of causing 5% or more damage to the pecan nut yield expected to be harvested. This is determined by sampling eggs and larval bores into the nutlets, randomly reviewing ten clusters per tree in at least 32 trees. An initial sampling should be done when there is between 963-979 HU accumulated, if two or more clusters are infested, before reviewing the 320 total clusters, this is considered as an indication that an economic damage will occur and that chemical control should be performed. If there is no damaged clusters, a second sampling is done after two or three days, when there is an accumulation of 1,007 HU, following the same procedure, if the infestation reaches the indicated threshold of action, the chemical control should be applied immediately, in order to avoid economical damage. Still, a third sampling can be done two days later and if three or more infested clusters are found, it is an indication that there may be economical damage, however, the decision to apply, will based on the producer judgment, based on whether the oviposition was delayed by weather conditions. The process can be summarized as:

$1^{st}$. Installation of pheromone traps four weeks before the first day of fertilizer spraying or as predicted by the method of accumulation of hours of heat from the point of 50% sprouting.

$2^{nd}$. A sampling of eggs is performed 7 to 10 days after first moth is caught, or 7 to 10 days before the accumulation of the required hours of heat. Check 10 clusters for eggs per tree in a sample of 30 to 32 trees, if two clusters per tree are infested it is considered that 5% of the harvest will be affected which is the minimum of harm to justify the use of insecticides.

$3^{rd}$. Monitor the color of the eggs daily to determine the time of hatching.

$4^{th}$. Apply insecticide two days after detecting the first hatching, or at the moment in which the entry of the larva into the nut is detected.

5°. Repeat the above steps in order to control the second generation. The control of the first and second generations affects the yield while the control of the third generation affects the quality of the crop.

The traditional method of control of this pest is based on the idea that the hibernating larva evolves according to the hours of heat it receives, so once the environmental temperature in autumn and winter does provide the heat necessary for its development, approximately 800 HU>78° F. (3.3° C.), the worm hatches from its cocoon. Under this theory, the larva is able to detect when spring arrives and emerge at the time the pecan nut tree gets out of its dormant state and has produced buds and shoots which the larvae can feed on.

The traditional method of monitoring, therefore, requires egg monitoring, installation of traps and monitoring of moths and finally the application of 3 to 5 treatments of insecticides. In addition to all these steps, success depends on the ability to determine the exact timing of insecticide application that allows attacking the larvae shortly after they hatched but before they enter the nuts. Once inside, the larvae are protected from insecticide treatments.

The present invention discloses for the first time in the state of the scientific and industrial art the possibility of anticipate the moment when the overwintering larva of pecan nut casebearer hatches from the cocoon while the pecan nut tree is still dormant, and said larva could be exterminated naturally. Premature hatching of larvae is caused by a series of artificially synthesized volatiles or semiochemicals that mimic the volatiles released naturally from the young shoots or buds of pecan nut tree. This technique results in a premature hatching of the hibernating larvae and therefore their possible death by starvation.

The characteristic details of this novel mixture and method for controlling insects of *Acrobasis nuxvorella* variety in plants of *Carya illinoiensis* variety are clearly detailed in the following description, FIGURE and the accompanying tables.

BRIEF DESCRIPTION OF DRAWINGS

FIG. 1 shows the behavior of the emergence of the larva of *Acrobasis nuxvorella*, according to the volatiles released from different shoots of *Carya illinoiensis*.

DETAILED DESCRIPTION OF THE INVENTION

The present invention relates to a mixture that causes premature hatching of larvae from *Acrobasis nuxvorella*, affecting plants of *Carya illinoiensis*, and which mixture comprises: Germacrene D, β-Caryophyllene, α-Caryophyllene, α-Cedrene, β-Cubebene, (+)-Cuparene, α-Cubebene, α-Elemene, (+)-δ-Cadinene, β-Gurjunene, Patchoulane, (+)-Longifolene, (+)-α-Longipinene and (+)-Valencene, for Western variety and the following mixture Germacrene D, β-Caryophyllene, α-Caryophyllene, α-Cedrene, β-Cubebene, (+)-Cuparene, (+)-δ-Cadinene, β-Gurjunene, Patchoulane, (+)-Longifolene, (+)-α-Longipinene and (+)-Valencene and D-Limonene for Wichita variety.

And the method to induce premature hatching of larvae from *Carya illinoiensis* on *Acrobasis nuxvorella* plants, wherein said method consists in applying the mixtures described above for each respective variety.

The compounds comprising the mixture were identified in shoots of 4 cm in length produced by Wichita or Western pecan nut trees just after emerging from its dormant state.

The experiment used for the determination of the results consisted in placing shoots 4, 2, 1 and a control (water), at different times for each of the varieties of pecan nut tree, in hermetically controlled containers, and injecting a carrier gas for the volatiles which were detected in a gas spectrometer, with the following compounds being determined and compared with the already registered compound registry number (CAS).

| No. | CAS Registry Number | Name | Sistematic name |
|---|---|---|---|
| 1 | 23986-74-5 | Germacrene D | 8-isopropyl-1-methyl-5-methylene-1,6-cyclodecadiene ($C_{15}H_{24}$) |
| 2 | 87-44-5 | β-Caryophyllene | Bicyclo[7.2.0]undec-4-ene,4,11,11-trimethyl-8-methylene-($C_{15}H_{24}$) |
| 3 | 6753-98-6 | α-Caryophyllene | 1,4,8-Cycloundecatriene,2,6,6,9-tetramethyl-Humulene ($C_{15}H_{24}$) |
| 4 | 469-61-4 | α-Cedrene | 1H-3a,7-methanoazulene, 2,3,4,7,8,8a-hexahydro-3,6,8,8-($C_{15}H_{24}$) |
| 5 | 13744-15-5 | β-Cubebene | 1H-cyclopenta[1,3]-cyclopropa[1,2]benzene,octahydro-7-methyl-3-methylene-4-(1-methylethyl-,[3as-(3aα,3bβ,4β,7α,7as*]- |
| 6 | 16982-00-6 | (+)-Cuparene | Benzene,1-methyl-4-(1,2,2-trimethylcyclopentyl)-,(r)-($C_{15}H_{22}$) |
| 7 | 17699-14-8 | α-Cubebene | 1H-cyclopenta[1,3]-cyclopropa[1,2]benzene, 3a,3b,4,5,6,7-hexahydro-3,7-dimethyl-4-(1-methylethyl)-,[3aS-(3aα,3bβ,4β,7α,7aS*)-(−)-]; ($C_{15}H_{24}$) |
| 8 | 5951-67-7 | α-Elemene | Cyclohexene,6-ethenyl-6-methyl-1-(1-methylethyl)-3-(1-methylethylidene)-,(s)-($C_{15}H_{24}$) |
| 9 | 483-76-1 | (+)-δ-Cadinene | Naphthalene,1,2,3,5,6,8a-hexahydro-4,7-dimethyl-1-(1-methylethyl-,(1s-cis)-($C_{15}H_{24}$) |
| 10 | 17334-55-3 | β-Gurjunene | 1H-ciclopropo(a)naphthalene, 1a,2,3,5,6,7,7a,7b-octahydro-1,1,7,7a-tetramethyl-,($C_{15}H_{24}$) |
| 11 | 25491-20-7 | Patchoulane | 1H-3a,7-methanoazulene,octahydro-1,4,9,9-tetramethyl ($C_{15}H_{26}$) |
| 12 | 475-20-7 | (+)-Longifolene | 1,4-methanoazulene,decahydro-4,8,8-trimethyl-9-methylene-, ($C_{15}H_{24}$) |
| 13 | 5989-08-2 | (+)-α-Longipinene | Tricyclo[5.4.0.0(2,8)]undec-9-ene, 2,6,6,9-tetramethyl-($C_{15}H_{24}$) |
| 14 | 4630-07-3 | (+)-Valencene | Naphthalene,1,2,3,5,6,7,8,8a-octahydro-1,8a-dimethyl-7 ($C_{15}H_{24}$) |
| 15 | 5989-27-5 | D-Limonene | Cyclohexene,1-methyl-4-(1-methylethenyl)-($C_{10}H_{16}$) |

After performing a bioassay consisting in determining which one of the set of volatile was able to awake *Acrobasis nuxvorella* (see FIG. 1). We can see from FIG. 1, that volatiles produced from Western variety shoots (BWE) of 4 cm, causes a greater need of emergency than any of the shoots from the variety Wichita (BWI) and from the control, in the insects.

On the other hand, the percentage of volatiles comprising the mixture was determined for both varieties Western and Wichita, as shown in the table below.

| No. | Compound | WE (%) | WI (%) |
|---|---|---|---|
| 1 | Germacrene D | 34.96 | 6.21 |
| 2 | β-Caryophyllene | 15.39 | 2.45 |
| 3 | α-Caryophyllene | 11.23 | 6.16 |
| 4 | α-Cedrene | 6.35 | 29.07 |
| 5 | β-Cubebene | 5.78 | 11.75 |
| 6 | (+)-Cuparene | 5.48 | 11.83 |
| 7 | α-Cubebene | 3.05 | 0 |
| 8 | α-Elemene | 2.55 | 0 |
| 9 | (+)-δ-Cadinene | 2.18 | 0.90 |
| 10 | β-Gurjunene | 1.84 | 0.38 |
| 11 | Patchoulane | 1.6 | 4.98 |
| 12 | (+)-Longifolene | 4.11 | 9.02 |
| 13 | (+)-α-Longipinene | 1.45 | 5.58 |
| 14 | (+)-Valencene | 2.46 | 3.93 |
| 15 | D-Limonene | 0 | 5.32 |

What is claimed is:

1. A mixture to cause premature hatching of larvae of *Acrobasis nuxvorella* in *Carya illinoiensis* plants, wherein said mixture comprises: Germacrene D present in 34.96%, β-Caryophyllene in 15.39%, α-Caryophyllene in 11.23%, α-Cedrene in 6.35%, β-Cubebene in 5.78%, (+)-Cuparene in 5.48%, α-Cubebene in 3.05%, α-Elemene in 2.55%, (+)-δ-Cadinene in 2.18%, β-Gurjuenene in 1.84%, Patchoulane in 1.6%, (+)-Longifolene in 4.11%, (+)-α-Longipinene in 1.45%, and (+)-Valencene in 2.46%.

2. A mixture to cause premature hatching of larvae of *Acrobasis nuxvorella* in *Carya illinoiensis* plants, wherein said mixture comprises: Germacrene D present in 6.25%, β-Caryophyllene in 2.45%, α-Caryophyllene in 6.16%, α-Cedrene in 29.07%, β-Cubebene in 11.75%, (+)-Cuparene in 11.83%, α-Cubebene, α-Elemene, (+)-δ-Cadinene in 0.90%, β-Gurjuenene in 0.38%, Patchoulane in 4.98%, (+)-Longifolene in 9.02%, (+)-α-Longipinene in 5.58%, and (+)-Valencene in 3.93%.

3. The mixture according to claim 2, wherein said mixture further comprises α-Cubebene, α-Elemene and D-timonene.

4. The mixture according to claim 3, wherein D-Limonene is present in 5.32%.

5. A method to cause premature hatching of larvae of *Acrobasis nuxvorella* in *Carya illinoiensis* plants, consisting of:
  spraying the mixture disclosed in claim 1 on pecan nut plants having hibernating larva when said larva has accumulated between 600 and 1,000 HU >38 ° F. (3.3° C.) and said plants have less than 50% of shooting following its dormant period,
  and wherein said spraying is done at least 1 month before the hatching of said larvae.

* * * * *

UNITED STATES PATENT AND TRADEMARK OFFICE
CERTIFICATE OF CORRECTION

PATENT NO. : 8,481,062 B2
APPLICATION NO. : 12/998563
DATED : July 9, 2013
INVENTOR(S) : Irasema del Carmen Vargas Arispuro et al.

It is certified that error appears in the above-identified patent and that said Letters Patent is hereby corrected as shown below:

In the Specification

In column 3, lines 34-35, replace the sentence "And the method to induce premature hatching of larvae from Carya illinoiensis on Acrobasis nuxvorella plants,..." with "And the method to induce premature hatching of larvae from Acrobasis nuxvorella on Carya illinoiensis plants,...".

In the Claims

In claim 3, column 5, line 8, replace the word "D-timonene" with "D-Limonene".

Signed and Sealed this
Twelfth Day of November, 2013

Teresa Stanek Rea
*Deputy Director of the United States Patent and Trademark Office*